United States Patent
Simons-Nikolova et al.

(10) Patent No.: US 9,524,654 B2
(45) Date of Patent: Dec. 20, 2016

(54) MODIFYING A PERSON'S EATING AND ACTIVITY HABITS

(71) Applicant: KONINKLIJKE PHILIPS N.V., Eindhoven (NL)

(72) Inventors: Mariana Simons-Nikolova, Bolton, MA (US); Maarten Peter Bodlaender, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 14/989,828

(22) Filed: Jan. 7, 2016

(65) Prior Publication Data

US 2016/0117952 A1    Apr. 28, 2016

Related U.S. Application Data

(63) Continuation of application No. 12/097,124, filed as application No. PCT/IB2006/054593 on Dec. 5, 2006, now Pat. No. 9,268,910.

(30) Foreign Application Priority Data

Dec. 15, 2005    (EP) .................................... 05112219

(51) Int. Cl.
*G09B 19/00* (2006.01)
*A61B 5/11* (2006.01)
(Continued)

(52) U.S. Cl.
CPC ......... *G09B 19/0092* (2013.01); *A61B 5/1123* (2013.01); *A61B 5/1128* (2013.01);
(Continued)

(58) Field of Classification Search
USPC ................ 382/100, 103, 106–107, 110, 118, 168,382/181, 184, 192–195, 201, 203, 209, 232,382/254, 274, 276, 282, 286–291, 305, 312; 600/590, 595, 587; 345/810; 340/573.1; 715/810; 434/127, 238

See application file for complete search history.

(56) References Cited

U.S. PATENT DOCUMENTS 6,028,960 A * 2/2000 Graf .................. G06K 9/00268 382/100
6,135,950 A    10/2000 Adams
(Continued)

FOREIGN PATENT DOCUMENTS

EP          1179799 A2    2/2002
WO    WO2004003848 A2    1/2004
(Continued)

*Primary Examiner* — Seyed Azarian
(74) *Attorney, Agent, or Firm* — Sherry Womack Austin

(57) ABSTRACT

A system for managing the food intake of a person comprises means for collecting information about food consumed by the subject, and means for providing feedback to the subject regarding the food consumed. It further comprises a sensor 57 for obtaining a signal related to the person and monitoring means for generating the information by performing a pattern recognition of the obtained signal for detecting whether the person is consuming food. The sensor comprises a camera and the pattern recognition comprises image processing. The image processing comprises the detection of a mouth and of a hand and of food. The system further comprises means for causing an audio/video-rendering device 56 to deliver the feedback. The camera is attached to the rendering device. The system further comprises means for identifying available rendering devices 56 arranged for being caused to deliver feedback.

19 Claims, 3 Drawing Sheets

(51) Int. Cl.
*G06F 19/00* (2011.01)
*G06T 7/20* (2006.01)
*G06F 3/048* (2013.01)

(52) U.S. Cl.
CPC ...... *G06F 19/3418* (2013.01); *G06F 19/3475* (2013.01); *G06T 7/20* (2013.01); *A61B 2562/0219* (2013.01)

(56) References Cited

U.S. PATENT DOCUMENTS

| | | | |
|---|---|---|---|
| 6,582,380 B2* | 6/2003 | Kazlausky | A61B 5/1118 600/595 |
| 7,914,468 B2* | 3/2011 | Shalon | A61B 5/0006 600/587 |
| 2001/0029319 A1 | 10/2001 | Kazlausky | |
| 2001/0049470 A1 | 12/2001 | Mault et al. | |
| 2002/0047867 A1* | 4/2002 | Mault | A61B 5/1118 715/810 |
| 2002/0109600 A1* | 8/2002 | Mault | A61B 5/1112 340/573.1 |
| 2003/0058111 A1* | 3/2003 | Lee | G06K 9/00342 340/573.1 |
| 2006/0064037 A1 | 3/2006 | Shalon | |

FOREIGN PATENT DOCUMENTS

| | | |
|---|---|---|
| WO | WO2004107227 A1 | 12/2004 |
| WO | WO2005013177 A2 | 2/2005 |
| WO | WO2006033104 A1 | 3/2006 |

* cited by examiner

MODIFYING A PERSON'S EATING AND ACTIVITY HABITS

CROSS-REFERENCE TO RELATED APPLICATIONS

This application is a Continuation under 35 U.S.C. §120 of U.S. patent application Ser. No. 12/097,124, filed Jun. 12, 2008, which claims the priority benefit under 35 U.S.C. §371 of international patent application no. PCT/IB2006/054593, filed Dec. 5, 2006, which claims the benefit of European Patent Application No. 05112219.0, filed on Dec. 15, 200513, the contents of which are incorporated herein by reference.

FIELD OF THE INVENTION

The invention relates to a system for changing the behavior of a subject, comprising
  means for collecting information about food consumed by the subject, and
  means for providing feedback to the subject regarding the food consumed.
The invention also relates to a method for managing the food intake of a person and to a computer program product.

BACKGROUND OF THE INVENTION

Overweight and obesity are growing problems, for example over 60% of the American population can be classified as overweight or obese. Weight gain occurs when a human has a higher energy intake (food) than energy expenditure (resting metabolic rate+activity). Since this misbalance causes the weight gain problem, many weight loss programs require that users log the food consumed and activities done in order to estimate the calorie balance.

Tables and equations exist for converting nutrition values and activities into calorie intake and expenditure, respectively. However, manual calorie counting is a cumbersome process requiring knowledge, time, effort, recording and discipline. Thus, calorie logging is a problem for many people and hence it is a challenge for researchers to find a solution therefore.

One of the most difficult and costly areas of healthcare involves the need for modifying an individual's lifestyle to prevent body disorders and/or chronic diseases. Bad eating and activity habits can strongly influence the risk of overweight and obesity, and therefore of co-morbidities like type II diabetes, heart disease, hypertension, and cancer.

In the international patent application WO 2005/013177 A2, a method, system, and apparatus is disclosed for health management monitoring. The system is designed to constantly monitor dynamic within-day energy balance deviations in real time. The patent application discloses a method for automatically determining an energy balance deviation. Thereto, it describes methods for determining energy (caloric) expenditure, methods for determining energy (caloric) intake, methods for determining within-day energy balance, and different sets of options on such devices for the general population, for public health, for fitness enthusiasts, for weight loss program attendees, and for research and clinical settings.

The energy intake can be predicted, among other ways, from the specific amounts and types of food consumed over a defined period of time. The basis of the nutric and caloric content of the foods consumed can be determined using freely available computerized databases. The within-day energy balance, defined as the ratio of energy intake and energy expenditure over a period of 24 hours or multiples of 24 hours, should not deviate too much from zero. According to the cited patent application, the energy balance should be considered for shorter periods during the day. Preferably, the within-day energy balance should be relatively close to zero. The system described in the cited patent application can notify users, such as through a series of beeps and/or vibrations, when within-day energy surpluses or energy deficits have exceeded the established bounds for pre-set goals. These cues can advise the user, for example, to eat or stop eating. The system can provide instantaneous feedback when the within-day energy balance deviates too much from zero, or it can provide a graphic output of a day's energy deficits and surplus using a device such as a personal computer. Energy intake, or food consumption, can be estimated through simple push-button descriptions of relative meal size and fat content, or through a pre-entered food list of foods commonly consumed by individual users or of foods recommended by weight loss programs. The system of the prior art requires the user to manually provide input about foods consumed. It turns out that the manual user input about foods consumed is not always correct.

SUMMARY OF THE INVENTION

It is an object of the invention to provide an improved system of the kind set forth in which more accurate information about foods consumed is provided to the system.
  This object is realized in that the system further comprises
    a sensor for obtaining a signal related to the person,
    monitoring means for generating the information by performing pattern recognition of the obtained signal for detecting whether the person is consuming food.
  A user may forget to provide input to the system when he or she is eating small amounts of food. Also, the user may not want to provide input to the system because it could be embarrassing to enter each small unit of food into the system. The user may also find it irritating to provide input every time a small snack or candy is consumed. Especially when performing a primary activity, such as watching television or reading a book, the subject is usually not inclined to provide user input about a secondary activity involving food consumption. The inventive system at least partly eliminates the need for manual input of food consumption, which results in more reliable information about food consumption.

According to another aspect of the invention, the sensor comprises a camera and the pattern recognition comprises image processing. Using a camera as the sensor is especially advantageous, because it can be active without requiring any user interaction. Image processing is an especially suitable form of pattern recognition when using camera images.

According to another aspect of the invention, the image processing comprises the detection of a mouth and of a hand. By detecting the mouth and a hand of the person, it becomes possible to detect a pattern related to food intake. It is advantageous to detect a hand near the mouth. It is especially advantageous to detect a movement of the hand or of the arm to and from the mouth. Advantageously, the system detects the chin and a movement of the chin, for example in combination with detecting whether the mouth is open or closed.

According to another aspect of the invention, the image processing comprises the detection of food. The detection of food further increases the accuracy of the system because food can only be consumed if it is detected near the person.

It is advantageous to detect a hand near food. It is more advantageous to detect a movement of the hand or of the arm to and from the food. It is especially advantageous to detect a movement of the hand or of the arm from the food to the mouth, to detect the food near the mouth, or to detect a movement of the food towards the mouth.

According to another aspect of the invention, the system further comprises means for causing an audio/video-rendering device to deliver the feedback. The feedback can comprise a visual or audible signal, but it can also comprise an audio and/or video clip, for example a voice message, a video message, and/or an animation, allowing the feedback to be given in a particularly pleasing or effective manner.

According to another aspect of the invention, the sensor is a camera attached to the rendering device. This aspect has at least two advantages. First, it is possible to detect whether the person is near the rendering device. Advantageously the system produces output on a rendering device only when the person is near the device. Second, when the person is watching a video program on the rendering device, the person has a predefined orientation with respect to the rendering device. By positioning the camera near the rendering device, the camera images comprise images of the person from a predictable viewing angle, usually frontal images. Having images of the person from a predictable viewing angle makes the image processing particularly easy to implement and particularly reliable. Alternatively, the position of the camera with respect to the rendering device is known and taken into account in the image processing. For example, images could be taken from the side of the person to easier detect the position of the hand and/or arm.

According to another aspect of the invention, it further comprises means for identifying available rendering devices arranged for being caused to deliver feedback, means for obtaining properties of the identified rendering devices, and means for selecting at least one of the rendering devices based on a predefined set of criteria related to the properties, wherein the means for causing a rendering device to deliver the feedback is arranged for causing the selected rendering device to deliver the feedback.

This aspect of the invention allows the system to select a device for providing the feedback that is related to an activity of the subject. For example, if the subject is watching for example a television show, a movie, or a music track, rendered on a device such as a television, a personal computer, or a radio, it is advantageous to use the same device for providing the feedback, because the attention of the subject is already focused on the rendering of that device, and a message delivered through that device is very likely to catch the attention of the subject. Among the identified devices, at least one device can be selected based on properties such as whether the modality has a display, the size of the display, or whether the modality has an amplifier.

According to another aspect of the invention, it further comprises means for obtaining at least one property related to the contents of an audio/video program being rendered, and the means for providing feedback operates in dependence on the property.

For example, it is advantageous to adapt the volume of the feedback message to the volume of the multimedia presentation. It is also advantageous to provide the feedback in a mood that is in agreement with the audio/video program. For example, if the audio/video program is related to a very sad story, it may be inappropriate to provide the feedback in a very funny way.

According to another aspect of the invention, the means for providing feedback is arranged for providing the feedback only during selected intervals. It is possible to select moments for providing feedback during intervals at which the subject is more receptive for the feedback. For example, the subject may be less receptive for feedback during an action scene, and in that case the system can wait with providing the feedback until the action scene has ended. By choosing selected moments for providing the feedback, the risk of annoying the subject is reduced.

According to another aspect of the invention, the sensor comprises a motion sensor or an accelerometer. This aspect of the invention improves the ability to detect a moving pattern related to food consumption. A motion sensor is useful to detect the level of activity and can be used to detect the movements related to food consumption. An accelerometer can be attached to, for example, the arm of the subject or to the clothing of the subject. It can be used to detect the accelerometer patterns related to food consumption, regardless of the position of the subject with respect to a camera or motion sensor. Advantageously, the accelerometer communicates with the modality by means of a wireless link, but it can also communicate via a wired link.

According to another aspect of the invention, it further comprises means for determining a total amount of food consumed or means for determining a trend in the amount of food consumed, wherein the means for providing feedback is arranged for periodically providing feedback relating to the total amount of food consumed or to the trend in the amount of food consumed. Preferably, the information is collected for a predefined time duration, for example a day or a week, and after the predefined time duration information is presented about the undesired eating habit, for example the amount of time spent eating behind the television each day in a week can be presented to a user in a graphical or textual representation. This aspect of the invention allows the user to periodically review his or her eating patterns and allows the user to be informed about progress in reaching his or her goals.

Preferably, the means for providing feedback is arranged for communicating the feedback at a time at which the monitoring means detects the consumption of food. By providing the feedback at a time the subject is still eating or drinking, the subject is helped to stop the eating or drinking sooner than if no feedback had been given. This aspect helps to reduce the risk of obesity by helping the subject to overcome undesirable habits such as excessive food consumption while watching television because the subject is confronted with feedback at the time the undesired behavior is taking place.

DETAILED DESCRIPTION OF THE INVENTION

Figure 1:
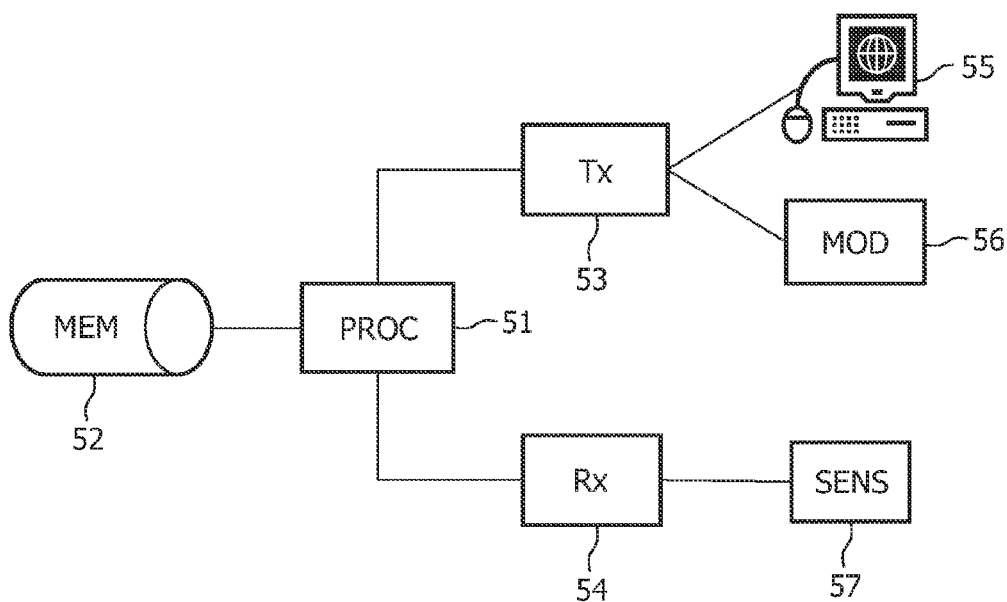
FIG. 1 shows a sketch of an embodiment of the invention.

FIG. 1 shows a schematic diagram of an embodiment of the present invention. It shows a microprocessor 51, a memory 52, receiving means 54, and transmitting means 53.

The microprocessor 51 performs instructions stored in the memory 52. It communicates with a sensor device 57, such as a camera, and with a modality 56 capable of presenting a multimedia presentation, such as for example a television, using the receiving means 54 and transmitting means 53. Advantageously, the receiving means 54 and transmitting means 53 are implemented using at least one communication standard such as USB, Firewire, Ethernet, or the WLAN standard IEEE 802.11. Using such communication standards allows the system to work with many different modalities 56, including different brands of television and different types of cameras. Advantageously, the communication means 53/54 also include video and audio communication means such as SCART or coax. The communication means 53/54 can also communicate eating patterns to a separate unit 55, for example a dedicated device, or a personal computer running suitable software. Such a device or personal computer may be used to display graphical or textual reports of the progress made in reducing the undesirable eating behavior.

The memory 52 is used to store instructions for making the processor 51 perform the inventive method. The memory 52 is also used to store the data needed for creating the reports of the progress made in reducing the undesirable eating behavior.

Figure 2:
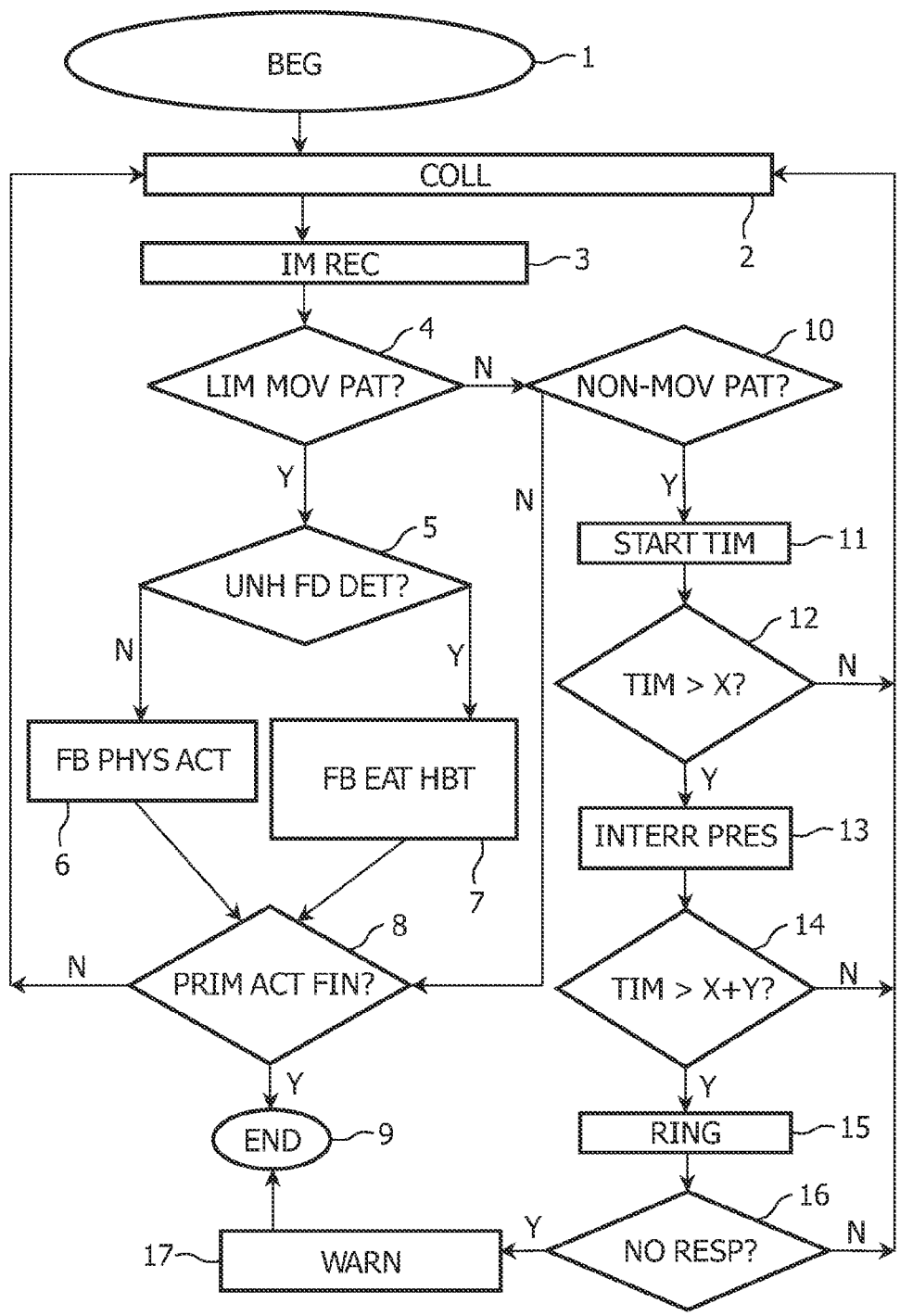
FIG. 2 shows a diagram of the steps involved in a method for modifying users eating and activity habits.

FIG. 2 shows a schematic diagram of an embodiment of the present invention. The method is started in step 1 when the subject has started a primary sedentary activity, such as watching a movie or reading a book, or for example a standing activity. In step 2, data from the monitoring devices are collected. The data can include images from a camera. The data can also include a signal from a motion sensor or for example accelerometer data collected by an accelerometer attached to for example the subject's wrist, or signals from two accelerometers, one attached to each wrist. In step 3, the data are analyzed for features correlated with a limited moving pattern. A limited moving pattern can indicate that the subject is watching a multimedia presentation. A limited moving pattern can also indicate that the subject is picking up food from a nearby table and consuming the food. If a limited moving pattern is found in step 4, the next step is to detect the presence of, possibly unhealthy, food in step 5. Unhealthy drinks such as beer or soda with sugar are also detected. Many different means can be used to detect the presence of food. For example, image processing of camera images may be used to detect the food itself or the packaging of the food. Alternatively, the packaging of the food may comprise detection means, such as a bar code or an RFID chip, allowing easy detection of the food on the table. In another embodiment, the food may be detected at the time it is retrieved from the cupboard or from the refrigerator, or the packaging may be arranged to transmit a signal that is received by the receiving means 54 when a package is opened by the user.

Alternatively, a more accurate analysis of the limited moving pattern may be used. If an accelerometer is attached to the wrist, the accelerometer patterns correlated with picking up food from the table and bringing the food into the mouth are detected and distinguished from random movements not related to eating and drinking. Preferably, multiple types of analysis are combined to achieve the greatest degree of reliability.

If both a limited moving pattern and unhealthy food are detected (steps 4 and 5), the system can provide feedback to the user about the undesired behavior in step 7. For example, the system can provide the feedback immediately upon detecting the undesired behavior, or it can provide the feedback only when the undesired behavior continues for a predetermined period. The preferred timing and the type of feedback depends on several factors, including the condition of the subject, his or her preferred diet, and his or her motivation to stop the undesired behavior. For example, if the subject is very obese and has a high degree of motivation to stop the undesired behavior, it is preferable to provide the feedback immediately upon detection of undesired behavior. If the subject is not motivated to stop snacking completely, but only wants to avoid eating continuously the whole evening, it is preferable to provide the feedback only after the undesired behavior has been detected for predetermined time duration. The system may also use the memory 52 to store the cumulative time the subject has been eating during a day, so that the system will only provide feedback when a predetermined daily limit has been exceeded.

Preferably, the feedback is presented in a way that has the greatest motivating effect on the long term. This is realized by feedback that is not irritating for the user. For example, a tone, a text message, or a voice message can be used. Advantageously, animated feedback can be used. The animation can involve a multi-media puppet. The animated puppet becomes gradually thicker indicating to the user that the snacking behavior will lead to weight gain. For multiple users involved in the sedentary activity, multiple puppets can appear on the screen animated with different images, or even personalized with the faces of the different users. The system can mirror the eating and activity habits of the individuals in the group by proper animation of the multiple puppets. More multimedia tools can be utilized such as speech, ring tones and text prompts.

Feedback can also be presented, for example, related to collected food intake information during a predefined period of time. For example, an animated puppet can be rendered that gradually collects animated foods representing foods consumed during the predefined period on an animated table. Confronting the users with a visual picture of total quantities and types of nutrients consumed has a profound effect over their awareness and is a step towards changing eating habits. The puppet can replace the unhealthy nutrients, for example food with a relatively high amount of saturated fat, salt and/or sugar, by healthy nutrients like fruits and vegetables, thereby educating the user about healthy meal decisions.

Advantageously, a tool kit comprising for example fruit and/or vegetable shaped objects of which, for example, the size, shape, or color can be controlled, is used to make the objects reflect the user's compliance to a healthy food intake pattern. The objects can be animated objects or real touchable objects comprising, for example, plastic material or textile. For example, if the user has an unhealthy food intake pattern the objects will be small and wrinkled, and if the user has a healthy food intake pattern, the objects will be large, and their shape and color will represent fruits or vegetables in good condition to be eaten. Other object shapes such as flower-shaped objects can also be used in a similar fashion.

If a limited moving pattern has been recognized in step 4, but no unhealthy food or drinks have been detected in step 5, and the limited moving pattern continues to be recognized for a predetermined time duration, the system proceeds to step 6, in which the subject is provided feedback about the need to engage in physical activity. This feedback may be provided in a way similar as in step 7. For example, an animated puppet can be shown from time to time that performs exercises to give some examples to the sedentary user of ways to achieve a sufficient level of activity. In case the users are children, for example detected automatically by detecting a children's TV program or a children's TV channel, the puppet can act as a kid's watcher that prompts the children to move from the sedentary activity to an active play after a children's TV program has finished.

In step 8, the system checks whether the subject is still performing the primary activity, and if so, the system continues at step 2. Alternatively, the system can continue monitoring the moving patterns of the subject independently of the primary activity.

In another embodiment, if a limited moving pattern is not detected in step 4, the system checks whether a non-moving pattern is detected in step 10, and if so, a timer is set in step 11. The non-moving pattern is associated with inactivity of the user for a period of time. Detecting this pattern is indicative for a user fallen asleep or a user with deteriorating health conditions. Correspondingly, the system can react by adapting the multimedia presentation or generating an alarm as follows. In step 12 it is checked if a non-moving pattern has been detected for longer than a predetermined period x, and if so, in step 13 the multimedia presentation is stopped by switching off the video source and/or the display, and control is taken of the audio source. Alternatively, the multimedia presentation is adapted to a sleeping condition of the subject, for example by lowering the volume or switching off or lowering a light source. In step 14 it is checked if the non-moving pattern is detected for a longer predetermined period x+y. In that case, in step 15 the audio source is used to produce a sound, for example a ring tone, in order to wake up the subject. Alternatively, another signal may be produced such as executing a multimedia presentation, increasing the volume, or turning on the light. Other ways to wake up the subject are obvious to the person skilled in the art. Moreover, the system may be arranged to produce a wake-up signal only at predetermined times, for example only at the time the subject should go to bed at night, or for example only at the time the subject should wake up in the morning.

If the subject wakes up, this is detected, for example, as a limited moving pattern in step 16, and the method continues from step 2. If a limited moving pattern is still not detected in step 16 after producing the ring tone, a warning message can be produced in step 17 in the form of, for example, a louder sound, an SMS, a voice mail message, or by causing any predetermined device to produce an alarm, such that another subject is warned about the condition of the first, monitored, subject.

Figure 3:
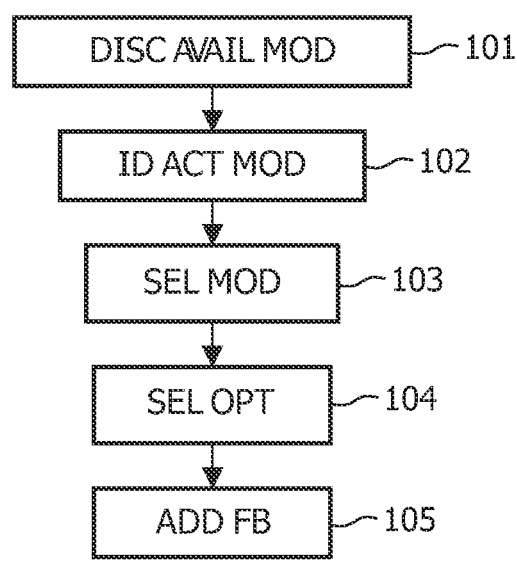
FIG. 3 shows a preferred embodiment of the invention.

A preferred embodiment is shown in FIG. 3. The available feedback modalities are discovered in step 101, for example through at least one UPnP/DLNA standardized "discovery" mechanism. In step 102, currently active modalities are identified, for example using at least one UPnP/DLNA standardized "control" mechanism to query the status of a modality, and optionally using content analysis techniques to detect which modalities are most perceptible by the user. In step 103, a number of modalities are selected to be used for generating the feedback message. The selection criteria can include the capabilities of individual modalities, such as video and/or audio generation, and the presence of the possibility to cause the modality to reproduce the feedback message. In step 104, a feedback-option is selected from a list of possible feedback-options, preferably sorted according to appropriateness, and the feedback-message is digitally enhanced to best match the primary activity, for example, the sound level is increased or the timing of the feedback is adapted such that it coincides with a period of low noise of the primary activity. Finally, in step 105, the feedback is added to the selected modality for example using overlay techniques in combination with an already active modality, or for example using a previously inactive modality. Such overlay techniques are known to the skilled artisan.

The feedback can be provided by replacing the image associated with the multimedia presentation with an image associated with the feedback, or by overlaying the image associated with the feedback on top of the image associated with the multimedia presentation. The feedback can be provided in the form of a text message. It can also be provided by means of a multimedia presentation such as for example an animated and/or pre-recorded video message or an audio message.

According to one aspect of the invention, it further comprises
 a sensor capable of detecting a non-moving pattern of the subject and generating data relating to the detected non-moving pattern, and
 means for causing a modality arranged for executing a multimedia presentation to adapt the multimedia presentation in dependence on the data relating to the detected non-moving pattern.

This aspect of the invention allows the invention to be used as a safety mechanism. A non-moving pattern can be related to for example a sleeping condition or a deteriorating health condition. In case of sleeping, it is appropriate to adapt the multimedia presentation to the sleeping condition, for example by reducing the volume. In case the modality also controls a light source, the system may for example be arranged to switch off the light after detecting a non-moving pattern.

According to another aspect of the invention, the means for causing the modality to adapt the multimedia presentation comprises means to stop the multimedia presentation. In case of a sleeping condition or a deteriorating health condition, it may be helpful to stop the multimedia presentation.

According to another aspect of the invention, it further comprises means for generating a sound in dependence on the data relating to the detected non-moving pattern. In case of a sleeping condition, it may be helpful to generate an alarm to wake up the subject. In case of a deteriorating health condition, it may be helpful to generate an alarm to let one or more other people know about the condition of the subject.

According to another aspect of the invention, it further comprises means for causing a device to generate an audible signal or a visible signal in dependence on the data relating to the detected non-moving pattern. For example, in case of a deteriorating health condition, it may be helpful to generate a signal using a device in the vicinity of one or more other people, to let the other people know about the condition of the subject. For example, the device can be in the same room as the subject, but advantageously it also works with the device in another room or further away, for example more than a kilometer away, from the subject.

It will be appreciated that the invention also extends to computer programs, particularly computer programs on or in a carrier, adapted for putting the invention into practice. The program may be in the form of source code, object code, a code intermediate source and object code such as partially compiled form, or in any other form suitable for use in the implementation of the method according to the invention. The carrier may be any entity or device capable of carrying the program. For example, the carrier may include a storage medium, such as a ROM, for example a CD ROM or a semiconductor ROM, or a magnetic recording medium, for example a floppy disc or hard disk. Further the carrier may be a transmissible carrier such as an electrical or optical signal, which may be conveyed via electrical or optical cable or by radio or other means. When the program is embodied in such a signal, the carrier may be constituted by such cable or other device or means. Alternatively, the carrier may be an integrated circuit in which the program is embedded, the integrated circuit being adapted for performing, or for use in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or steps other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. An apparatus, comprising:
a microprocessor configured to:
receive image data of a food;
receive data corresponding to movement by a subject relative to the food;
based on the image data, determine that the food is unhealthy;
based on the determination that the food is unhealthy and further based on a determination by the microprocessor that the data about the movement by the subject corresponds to a limited movement pattern, determine that the subject is engaged in unhealthy behavior;
based on the determination of the unhealthy behavior, provide feedback related to the unhealthy behavior; and
store in memory the image data and the data corresponding to movement by the subject over a predefined time duration and provide the feedback after the predefined time duration.

2. The apparatus of claim 1, wherein the predefined time duration comprises one of a day or week.

3. The apparatus of claim 1, wherein the feedback comprises a visual message, audible message, or a combination of a visual and audible message.

4. The apparatus of claim 1, wherein the microprocessor is further configured to receive data corresponding to a location where the subject is consuming the food relative to a first device comprising an audio device, visual device, or a combination of an audio and visual rendering device.

5. The apparatus of claim 1, wherein the microprocessor is further configured to:
receive data corresponding to a property related to contents of a multimedia presentation presented on the first device; and
provide the feedback in dependence on the property.

6. The apparatus of claim 5, wherein the microprocessor is further configured to provide the feedback at an adjusted volume based on a volume of the multimedia presentation.

7. The apparatus of claim 6, wherein the microprocessor is further configured to adjust a presentation time of the feedback depending on a mood conveyed by the multimedia presentation.

8. The apparatus of claim 6, wherein the microprocessor is further configured to:
provide the feedback only at a select interval during presentation of the multimedia presentation; and
determine the select interval based on a determination by the microprocessor as to when the subject is anticipated to be more receptive to the feedback.

9. The apparatus of claim 1, wherein the microprocessor is further configured to provide the feedback proximal in time to when the subject is consuming the food or periodically.

10. The apparatus of claim 1, wherein the microprocessor is configured to provide the feedback immediately upon the determination or after determining that the unhealthy behavior continues for a predetermined period of time.

11. The apparatus of claim 1, wherein the microprocessor is configured to provide the feedback according to an adaptable time of presentation and adaptable content of a message corresponding to the feedback related to the unhealthy behavior.

12. The apparatus of claim 11, wherein the microprocessor is configured to adapt the content based on a condition of the subject.

13. The apparatus of claim 11, wherein the microprocessor is configured to adapt the content based on a preferred diet of the subject.

14. The apparatus of claim 11, wherein the microprocessor is configured to adapt the content based on a motivation of the subject to stop the unhealthy behavior.

15. The apparatus of claim 1, wherein the microprocessor is further configured to provide the feedback as a message conveying any one or a combination of an identity of the consumed foods, quantities of the consumed foods, and types of nutrients making up the consumed foods.

16. The apparatus of claim 1, wherein the microprocessor is further configured to provide the feedback as a message conveying a healthy alternative to the consumed food.

17. A non-transitory computer readable medium comprising executable code that, when executed by a microprocessor, causes the microprocessor to:
receive image data of a food;
receive data corresponding to movement by a subject relative to the food;
determine that the data about the movement by the subject corresponds to a limited movement pattern;
based on the image data, determine that the food consumed by the subject is unhealthy;
based on the determinations that the food is unhealthy and the movement corresponds to the limited movement pattern, determine that the subject is engaged in unhealthy behavior;
based on the determination of the unhealthy behavior, provide feedback related to the unhealthy behavior; and
store in memory the image data and the data corresponding to movement by the subject over a predefined time duration and provide the feedback after the predefined time duration.

18. The non-transitory computer readable medium of claim 17, further comprising executable code that, when executed by the microprocessor, causes the microprocessor to:
receive data corresponding to a location where the subject is consuming the food relative to a first device comprising an audio device, visual device, or a combination of an audio and visual rendering device;

receive data corresponding to a property related to contents of a multimedia presentation presented on the first device; and provide the feedback in dependence on the property.

19. A method, comprising:

at a microprocessor:

receiving image data of a food;

receiving data corresponding to movement by the subject consuming the food;

determining that the data about the movement by the subject corresponds to a limited movement pattern;

determining that the food consumed by the subject is unhealthy based on the image data;

determining that the subject is engaged in unhealthy behavior based on the determinations that the food is unhealthy and the movement corresponds to the limited movement pattern;

providing feedback related to the unhealthy behavior based on the determination of the unhealthy behavior; and storing in memory the image data and the data corresponding to movement by the subject over a predefined time duration and provide the feedback after the predefined time duration.

* * * * *